United States Patent
Yang

(10) Patent No.: US 9,568,721 B2
(45) Date of Patent: Feb. 14, 2017

(54) FLUORESCENT BIOLOGICAL SAMPLE OPERATING AND MONITORING SYSTEM

(71) Applicant: Lumos Technology Co., Ltd., Taipei (TW)

(72) Inventor: Chih-Yi Yang, Taipei (TW)

(73) Assignee: Lumos Technology Co., Ltd., Taipei (TW)

( * ) Notice: Subject to any disclaimer, the term of this patent is extended or adjusted under 35 U.S.C. 154(b) by 94 days.

(21) Appl. No.: 14/716,438

(22) Filed: May 19, 2015

(65) Prior Publication Data

US 2015/0330901 A1    Nov. 19, 2015

(30) Foreign Application Priority Data

May 19, 2014   (CN) .......................... 2014 1 0210881

(51) Int. Cl.
*G01N 21/64* (2006.01)
*G02B 21/06* (2006.01)
*G02B 21/16* (2006.01)
*G02B 21/36* (2006.01)

(52) U.S. Cl.
CPC ........... *G02B 21/06* (2013.01); *G01N 21/6458* (2013.01); *G01N 21/6486* (2013.01); *G02B 21/16* (2013.01); *G02B 21/361* (2013.01); *G01N 2201/062* (2013.01); *G01N 2201/064* (2013.01)

(58) Field of Classification Search
CPC ... A61B 1/0638; A61B 5/0071; A61B 5/0086; G01N 21/6456; G01N 21/6458; G01N 21/6486; G01N 2201/062; G01N 2201/064
See application file for complete search history.

(56) References Cited

U.S. PATENT DOCUMENTS

| | | | | |
|---|---|---|---|---|
| 8,345,941 B2* | 1/2013 | Oda | ................... | G01N 21/6456 348/135 |
| 8,842,173 B2* | 9/2014 | Hizume | ............. | G01N 21/6456 345/426 |
| 2003/0214581 A1* | 11/2003 | Ikami | ........................ | G06T 5/00 348/86 |
| 2011/0117025 A1* | 5/2011 | Dacosta | ............... | A61B 5/0059 424/9.6 |
| 2011/0270092 A1* | 11/2011 | Kang | ................... | A61B 5/0071 600/476 |
| 2014/0276008 A1* | 9/2014 | Steinbach | ............ | A61B 5/0071 600/424 |

\* cited by examiner

*Primary Examiner* — Marcus Taningco
(74) *Attorney, Agent, or Firm* — Wang Law Firm, Inc.

(57) ABSTRACT

A fluorescent biological sample operating and monitoring system for restricting the range of movement of a biological sample to facilitate observation. The system includes: a base formed with a predetermined observation position; a shield formed with an operation opening and cooperating with the base to define a light shielding cavity; an infrared illuminating device for illuminating the predetermined observation position; a low-angle excitation light source device including an excitation light source that emits light in a direction oriented toward the predetermined observation position and of a wavelength smaller than that of light emitted by the infrared illuminating device; and an observation display device including an image capturing device having a lens disposed within the shield for capturing an infrared image and oriented toward the predetermined observation position, and an image display.

9 Claims, 6 Drawing Sheets

FLUORESCENT BIOLOGICAL SAMPLE OPERATING AND MONITORING SYSTEM

FIELD OF THE INVENTION

The present invention relates to a fluorescent biological sample operating and monitoring system that prevents an operator from inadvertently damaging the integrity of biological samples due to accidence.

DESCRIPTION OF THE RELATED ART

In addition to having applications in cell analysis and tracking in biological research, fluorescence technology has been used in substantive applications as industrial inspection, false currency recognition, and criminal identification in recent years. As such, fluorescence microscopic image capturing is becoming more and more important. In a conventional fluorescence microscope, a high-frequency light beam is irradiated on an object having a fluorescent characteristic, such as an anti-counterfeiting security thread in a banknote or a suspected blood stain in a crime scene to thereby excite a fluorescence emission of a relatively low frequency. The fluorescence emission is then directed through a filter assembly, so that a clear fluorescent image of the security thread or the blood stain may be obtained and captured. In the field of biotechnology, studies in transgenic organisms often involve the introduction of a genetic material that is capable of expressing a fluorescent protein in organisms. The presence or absence of the expressed fluorescent protein in the organisms can help confirm whether or not an exogenous gene of interest has been introduced into the organisms and the fluorescent protein serves as a useful marker for tracing the transgenic organisms. In other words, fluorescence can be observed only when the exogenous gene of interest is successfully introduced into the organisms and expressed therein. Otherwise, no fluorescence will occur.

Many fluorescent biological samples, such as experimental mice, would move around and not stay still for observation by an operator. Conventional observation apparatuses for observing fluorescent response in experimental mice are not without drawbacks. For instance, the space for the mouse to move around is too large so that it may go to a blind spot of the observation lens and is thus hidden from view. Fluorescent zebrafish (*Danio rerio*) have been under extensive study in recent years primarily because they can reproduce rapidly and in great numbers, and have characteristics resembling those of human organs. They have even been used in the study of diseases, drug screening, toxicity tests, and the like. However, as zebrafish are used as an in vivo model in experiments, the effect of operating time and experimental environment thereon must be taken into consideration when conducting a fluorescence microscopic experiment. Operation by an inexperienced operator or bad luck may cause the experiment to fail.

Because zebrafish are very small in size, even smaller than a sesame seed, if any inadvertent errors occur during transfer or placement of the zebrafish, too many or too few zebrafish may be dropped from a pipette, which may cause the operation result to be inaccurate. On the other hand, as the fluorescence emitted by an experimental target in a fluorescence experiment is too weak, the intensity difference is very obvious in comparison with either incident light or direct reflected light, or even scattered reflected light. A little external stray light may cause serious interference on the experiment. Therefore, currently, in fluorescence experiments, external background light has to be completed isolated. Moreover, optical devices such as filter lenses need to be used to filter out the wavelength of the original incident light, permitting emission of only light of the fluorescence wavelength. As such, the environment is virtually completely dark during the process of the experiment, lit only by the extraordinarily weak fluorescence. If no fluorescence response is detected, it is impossible to confirm whether the lack of response is due to the zebrafish's failure to produce fluorescence or because no zebrafish were placed in the observation apparatus in the first place.

In addition, if the internal organs of a fluorescent biological sample are to be observed for the purpose of conducting an operation or dissection, blind operation or operation under weak fluorescent irradiation cannot allow the operator to be sufficiently aware of the three-dimensional spatial relationship of the internal organs. In this regard, the operator primarily relies upon his/her sense of touch or accumulated experience, and determines the state or progress of the operation by feeling around or groping. Thus, errors or even self injury may occur during the operation or dissection, thereby adversely affecting the efficiency and accuracy of the experiment.

SUMMARY OF THE INVENTION

Accordingly, the present invention aims to provide a fluorescent biological sample operating and monitoring system that provides uniform and sufficient illumination and that is convenient to operate, while preventing interference from external strong light and stray light and increasing the restriction on the range of movement of the fluorescent biological sample. Furthermore, by providing a low-angle excitation light source, the prior art drawback of the reflected light being more intense than the fluorescence to be observed in experiments due to direct reflection of the light source can be obviated, so that the experiment process will not be interrupted by other matters, thereby enhancing the overall efficiency of the experiment, operational convenience, and safety.

In an aspect disclosed herein is a fluorescent biological sample operating and monitoring system that utilizes infrared illumination to prevent blind operation to thereby enhance accuracy in experiments.

In another aspect disclosed herein is a fluorescent biological sample operating and monitoring system that utilizes a shield to ward off interference from external strong light and stray light to thereby enhance the quality of fluorescence microscopic imaging.

In yet another aspect disclosed herein is a fluorescent biological sample operating and monitoring system that is formed with an isolation space so that a fluorescent biological sample cannot move away from a predetermined observation position, thereby enhancing the success rate of experiments.

In still another aspect disclosed herein is a fluorescent biological sample operating and monitoring system formed with an isolation space, which utilizes a low-angle light source to obviate the prior art drawback of the reflected light being more intense than the fluorescence to be visually observed by the observer or to be optically captured by a photographic device in experiments, due to direct reflection of light emitted from the light source.

To achieve the aforesaid objects, the present invention provides a fluorescent biological sample operating and monitoring system for restricting the range of movement of at least one fluorescent biological sample so as to facilitate observation of the fluorescent biological sample using the fluorescent biological sample operating and monitoring system. The fluorescent biological sample operating and monitoring system includes: a base formed with a predetermined observation position; a shield corresponding to the base and formed with at least one operation opening, the shield cooperating with the base to define a light shielding cavity; an infrared illuminating device for illuminating the predetermined observation position with infrared light; a low-angle excitation light source device including a plurality of excitation light sources that emit light at a low angle in a direction oriented toward the predetermined observation position, the light emitted by the excitation light sources having a wavelength smaller than that emitted by the infrared illuminating device; and an observation display device including: at least one image capturing device, the image capturing device having a lens disposed in the shield and oriented toward the predetermined observation position for capturing an infrared image; and at least one image display for displaying the infrared image of the predetermined observation position captured by the image capturing device to the outside of said shield.

Therefore, the fluorescent biological sample operating and monitoring system disclosed in the present invention can, through use of a low-angle light source, overcome the drawback of the reflected light being more intense than the fluorescence to be observed in experiments due to direct reflection of a light source. Moreover, the need in the prior art for multiple filter lenses to filter off reflected light caused by direct reflection, which inevitably results in filtering off of some fluorescence to be observed in experiments, and for a lens with a magnification factor to permit naked-eye observation of fluorescence entails high cost as the lenses are expensive. By employing low-angle illumination to eliminate direct reflection of light to save lens costs, the present invention provides a low-cost system. In addition, to ensure the efficiency of experiments, there is provided a switching device to allow the operator to freely switch between an operating state and a monitoring state to enhance manipulation intuitiveness. Furthermore, an infrared lighting device is additionally provided within the shield so that experiments will not be conducted in a substantially blind state, and the movement of the fluorescent biological sample can be accurately controlled to enhance the accuracy of experiments.

BRIEF DESCRIPTION OF THE DRAWINGS

The above and other objects, features and effects of the invention will become apparent with reference to the following description of the preferred embodiments taken in conjunction with the accompanying drawings, wherein like numerals designate similar parts.

DETAILED DESCRIPTION OF THE INVENTION

Figure 1:
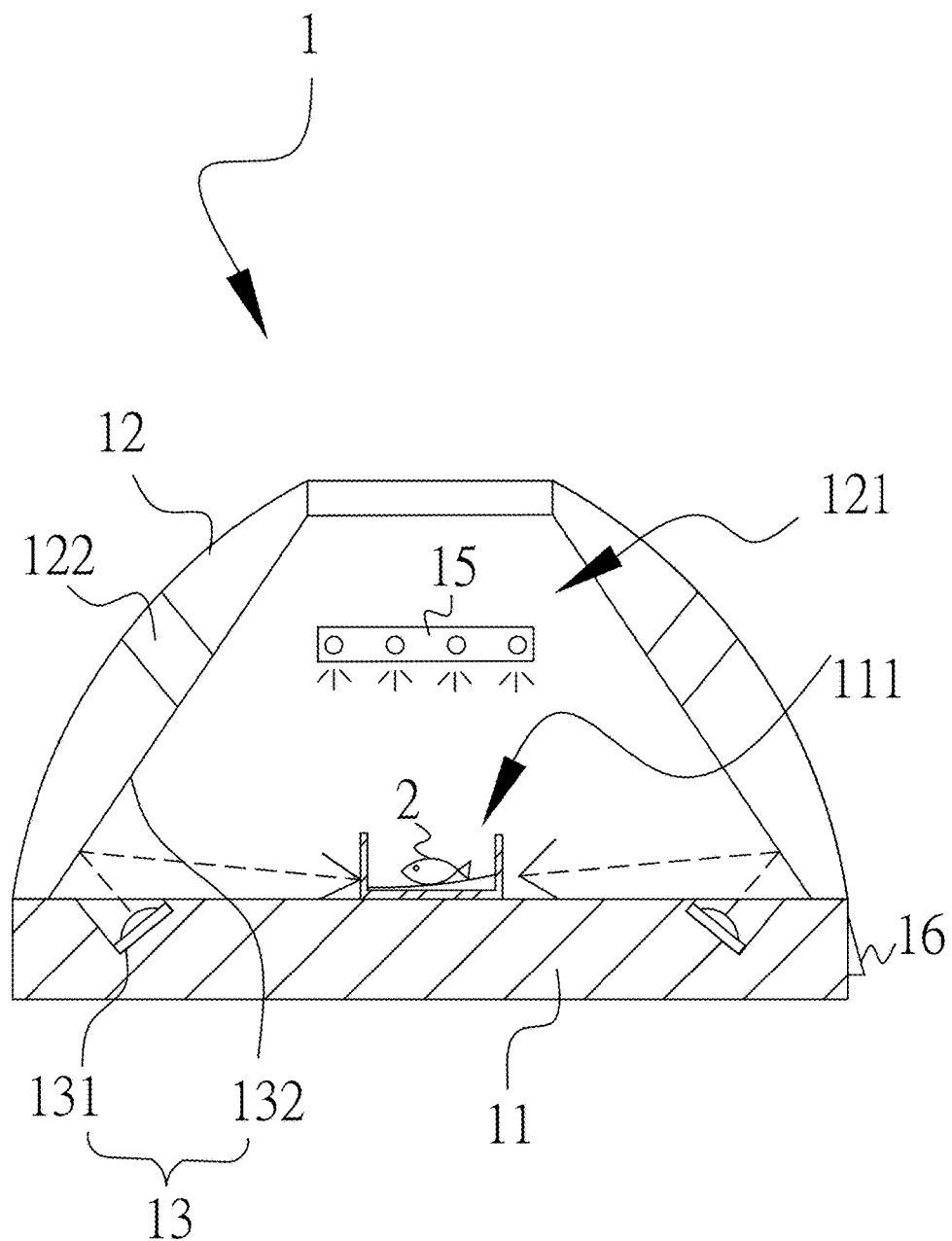
FIG. 1 is a sectional view of a fluorescent biological sample operating and monitoring system according to a first preferred embodiment of the present invention, illustrating that the range of movement of zebrafish is restricted.
Figure 2:
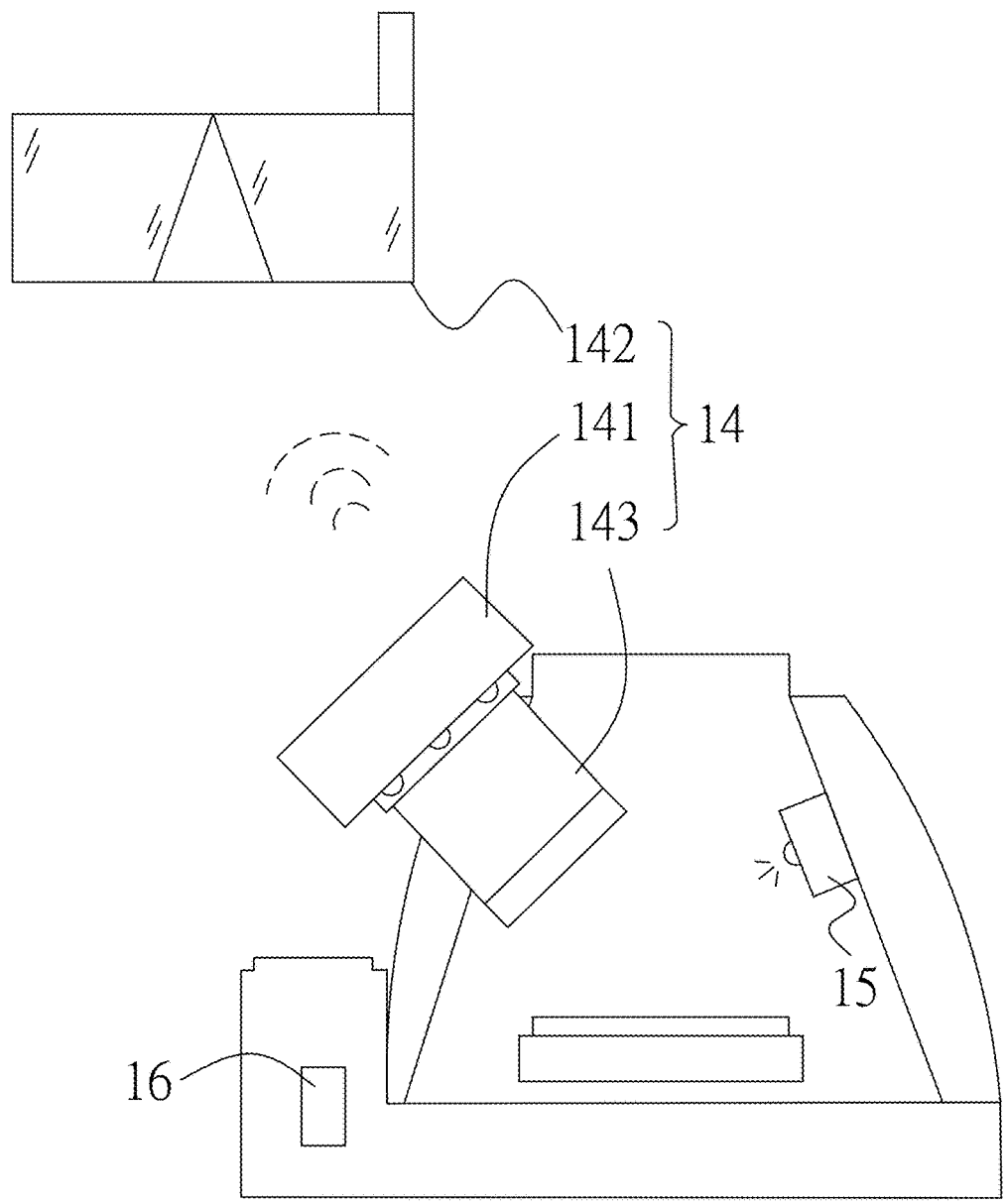
FIG. 2 is a schematic view of an observation display device shown in FIG. 1, illustrating that, through a switching device and a dynamic camera transmitting different signals, a display mask is caused to display different images.

As shown in FIGS. 1 and 2, a fluorescent biological sample operating and monitoring system 1 according to a first preferred embodiment of the present invention includes a base 11, a shield 12, and a low-angle excitation light source device 13. The base 11 is formed with a predetermined observation position, which is a predetermined movement region for the fluorescent biological sample on the base 11. In this embodiment, the fluorescent biological sample is exemplified as zebrafish 2. The predetermined movement region is exemplified as a transparent petri-dish (not denoted by reference numeral). The base 11 and the shield 12 cooperatively define a light shielding cavity 121 to block out external light that may interfere with operation and observation during experiments and to restrict the maximum range of movement of the live fluorescent biological sample. The light shielding cavity 121 in this embodiment is not completely closed, and has two operation openings 122 disposed respectively at left and right sides thereof to permit an operator to insert his/her hands into the light shielding cavity 121 to conduct experiments. To prevent relatively large live fluorescent biological samples from escaping from the light shielding cavity 121 through the operation openings 122, a set of detachable mechanical arms (not shown) can be alternatively disposed at the positions of the operation openings 122, respectively, to facilitate manipulation of the mechanical arms by the operator for conducting relevant experiments.

By virtue of the base 11 and the enclosing shield 12, and by providing a drape (not shown) at the left and right operation openings 122 (or using the arms of the operator instead), external light can be prevented from entering into the light shielding cavity 121, thereby substantially reducing any background stray light into the light shielding cavity 121. The low-angle excitation light source device 13 includes an excitation light source 131 having light-emitting elements, such as light-emitting diodes. In this embodiment, the excitation light source 131 of the low-angle excitation light source device 13 is disposed on the base 11, and is configured to emit a light beam obliquely upward. The low-excitation light source device 13 further includes a reflecting portion 132 formed at an inner side of the shield 12 to reflect the light beam emitted by the excitation light source 131 to the predetermined observation position 111 on the base 11.

To enhance the operational convenience of experiments, the fluorescent biological sample operating and monitoring system 1 in this embodiment further includes an observation display device 14. The observation display device 14 includes an image capturing element, exemplified as a dynamic camera 141, and an image display, exemplified as a display mask 142. The dynamic camera 141 has a lens 143 disposed within the shield 12 and oriented toward the predetermined observation position 111 for capturing an infrared image of the zebrafish 2 irradiated by an infrared illuminating device 15. The dynamic camera 141 has a receivable wavelength range encompassing the wavelength of light emitted by the infrared illuminating device 15, and the wavelength of fluorescence emitted by the zebrafish 2 irradiated by light from the low-angle excitation light source 131. Since the wavelength of the light emitted by the infrared lighting device 15 is longer than the wavelength of light emitted by the low-angle excitation light source device 13 and is within the range of near-infrared wavelength, it is not visible to the naked eye. With the aid of the display mask 142 which displays the infrared image captured by the dynamic camera 141, the operator can conduct precise alignment in a three-dimensional space, thereby preventing error in reading space.

In addition, the fluorescent biological sample operating and monitoring system 1 according to this embodiment further includes a switching device 16 to allow the operator to freely perform switching. When it is necessary to anesthetize the zebrafish 2 or to confirm whether the zebrafish 2 is placed at the predetermined observation position 111, the operator can switch the switching device 16 to, for example, an operating state, wherein the infrared illuminating device 15 disposed at the inner side of the shield 12 is enabled to emit light, and the dynamic camera 141 synchronously starts capturing infrared images of the zebrafish 2. The infrared images captured by the dynamic camera 141 is transmitted using, for example, Bluetooth technology to the display mask 142 for display thereon so that, during dissection of the zebrafish 2, the operator can clearly observe the progress of the dissection procedure by virtue of the infrared illumination, thereby reducing error rate in experiments. On the other hand, after it has been confirmed that the dissection procedure is completed, the switching device 16 can be started once again to switch to, for example, a monitoring state, wherein the infrared light emitted by the infrared illuminating device 15 is out, and the excitation light source 131 on the base 11 emits light instead. The light emitted by the excitation light source 131 is reflected to irradiate on the fluorescent biological sample. The dynamic camera 141 then takes fluorescent images of the fluorescent biological sample for transmission to the display mask 142 so that the operator can clearly observe any fluorescence response in the internal organs of the zebrafish 2 to thereby confirm the result of the fluorescence experiment.

In general, as the base excels the display mask in heat dissipating effect and has a wider selection of heat dissipating materials, the arrangement of the excitation light source device on the base facilitates heat dissipation and reduces the rate of damage to the animal protein of the zebrafish irradiated by the excitation light due to rise in temperature. In this embodiment, the fluorescent biological sample operating and monitoring system is an integrated independent structure. After finishing observation, the operator can directly dismantle the fluorescent biological sample operating and monitoring system to wash the base and the shield independently, thereby enhancing cleaning convenience. While the excitation light source of the low-angle excitation light source device is disposed on the base in this embodiment, it will be apparent to those skilled in the art that the excitation light source of the low-angle excitation light source device may be disposed on the shield like the infrared illuminating device without affecting the implementation of the present invention.

It can be appreciated from the foregoing description of the embodiment that the present invention has at least the following characterizing features. By virtue of the low-angle excitation light source device, the drawback that the reflected light is more intense than the fluorescence to be observed in experiments due to direct reflection of a light source can be overcome. Moreover, regarding the need in the prior art for multiple filter lenses to filter off reflected light caused by direct reflection, which inevitably results in filtering off of some fluorescence to be observed in experiments, and for a lens with a magnification factor to permit naked-eye observation of fluorescence which entails high cost as the lenses are expensive, by employing low-angle illumination to eliminate direct reflection of light to save lens costs, the present invention provides a low-cost system. In addition, to ensure the efficiency of experiments, the switching device in this embodiment allows the operator to freely switch between an operating state and a monitoring state to enhance operational convenience in experiments. Furthermore, by virtue of the arrangement of the infrared illuminating device within the shield, the dynamic camera, and the display mask, infrared images can be captured by the dynamic camera for transmission to the display mask via Bluetooth transmission for display, so that the operator can have a clear sense of space, thereby preventing errors in reading space.

Figure 3:
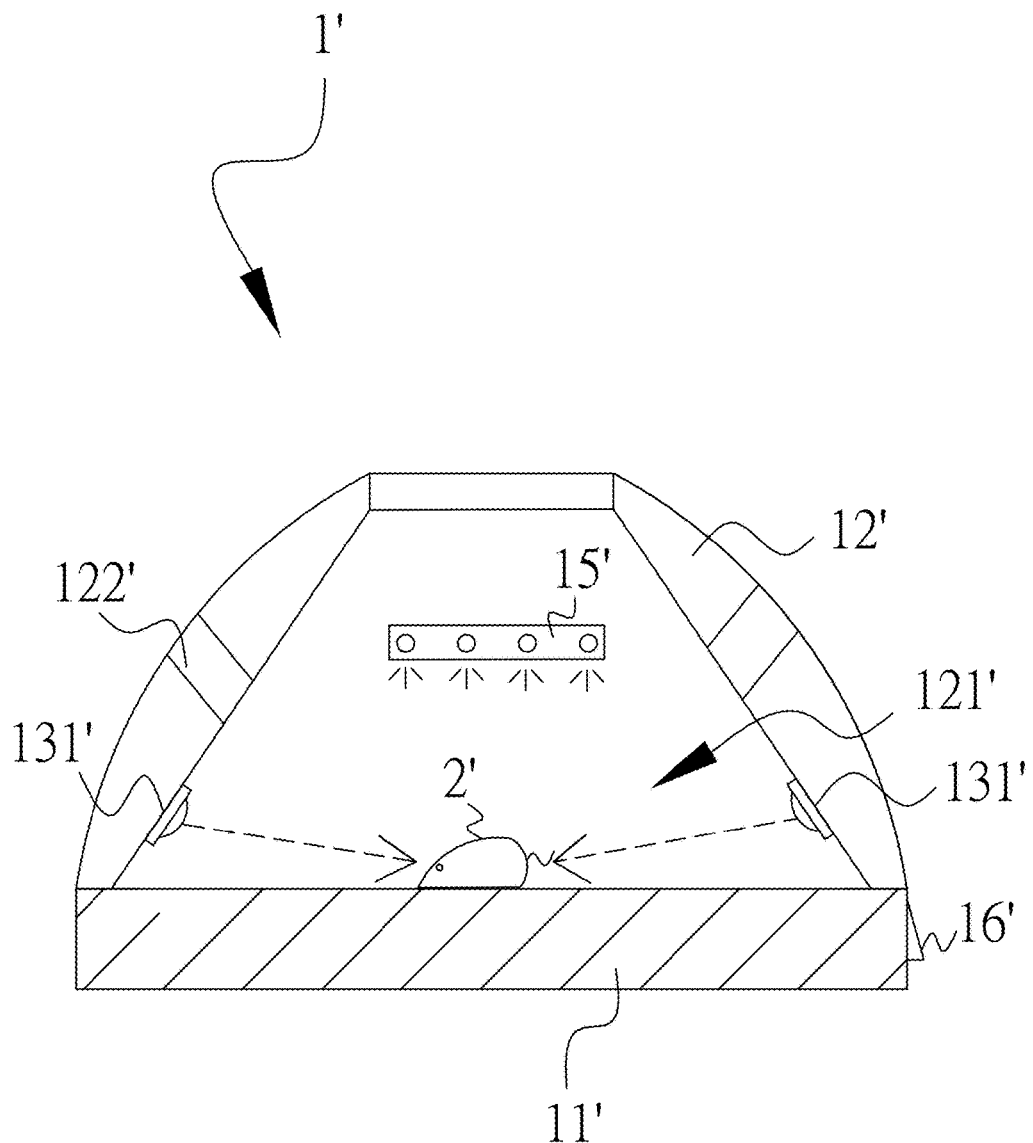
FIG. 3 is a sectional view of the fluorescent biological sample operating and monitoring system according to a second preferred embodiment of the present invention, illustrating that the range of movement of a mouse is restricted by a shield.
Figure 4:
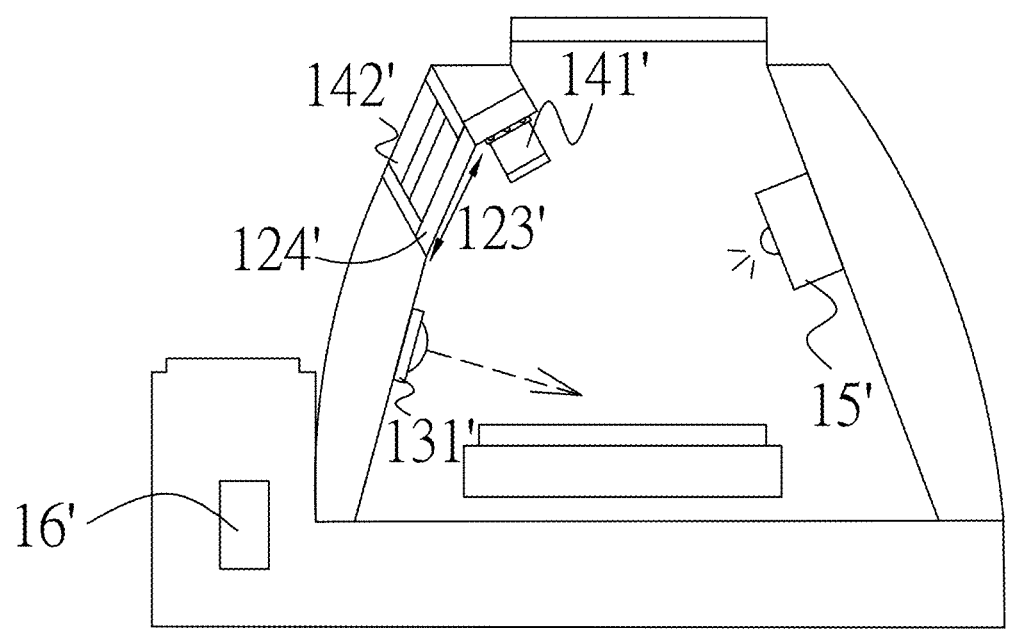
FIG. 4 is a sectional view of a fluorescent biological sample operating and monitoring system according to the second preferred embodiment, illustrating that a filter lens and a liquid crystal display screen are disposed above an observation opening to facilitate observation and operation, and that, through a switching device and a dynamic camera transmitting different signals, the liquid crystal display screen is caused to switch between a light transmissive state and a no-light transmissive state.

FIGS. 3 and 4 show a fluorescent biological sample operating and monitoring system 1' according to a second preferred embodiment of the present invention. Similar to the first preferred embodiment, a shield 12' and a base 11' cooperatively define a light shielding cavity 121' to block out external light that may interfere with observation in experiments. In addition to having operation openings 122' as in the first preferred embodiment, the light shielding cavity 121' has an observation opening 123' provided at the side of the light shielding cavity 121' that faces the operator. Moreover, to prevent the wavelength emitted by an excitation light source 131' from escaping through the observation opening 123', a filter lens 124' is further disposed on the observation opining 123', so that the light beam emitted by the excitation light source 131' cannot pass and affect the observation results.

In addition, the image capturing device of the first preferred embodiment is also exemplified as a dynamic camera 141' in this embodiment. In this embodiment, the dynamic camera 141' has a receivable wavelength range encompassing the wavelength of light emitted by an infrared illuminating device 15' as in the first preferred embodiment, and is provided adjacent to the observation opening 123' to provide a similar observation angle. In this embodiment, the image display is exemplified as a transmissive organic light-emitting diode (OLED) display screen 142'. In this embodiment, the OLED display screen 142' is directly disposed behind the filter lens 124' and cooperates with a switching device 16' similar to that of the first preferred embodiment. When the switching device 16' is switched to an operating state, the infrared illuminating device 15' is enabled to emit infrared light that irradiates a fluorescent biological sample, exemplified as a mouse 2' in this embodiment. The dynamic camera 141' captures an infrared image of the mouse 2' and outputs an image display signal to the OLED display screen 142'. After the OLED display screen 142' has received the image display signal, cells thereof will emit light to display the infrared image captured by the dynamic camera 141' to enable the operator to carry out an operation or experiment based on the image captured by the dynamic camera 141'.

When the switching device 16' is switched to the monitoring state, the OLED display screen 142' is switched to a no-light emitting light transmissive state, and the excitation light and fluorescence in the light shielding cavity 121' escape to the outside through the observation opening 123'. Due to the function of the filter lens 124', the light beam emitted by the excitation light source 131', being limited to a specific wavelength, will be filtered off, regardless of whether it is directly reflected light or scatteredly reflected light, so that it is hardly emitted. The considerable reduction in penetration rate of the excitation light allows the operator to directly observe the fluorescence of the mouse 2' from the observation opening 123' through the transmission OLED display 142' and the filter lens 124'. While the excitation light source of the low-angle excitation light source device is disposed within the shield, it is apparent to those skilled in the art that the excitation light source of the low-angle excitation light source device may, like the first preferred embodiment, be disposed on the base to achieve similar functions without affecting the implementation of this embodiment.

Figure 5:
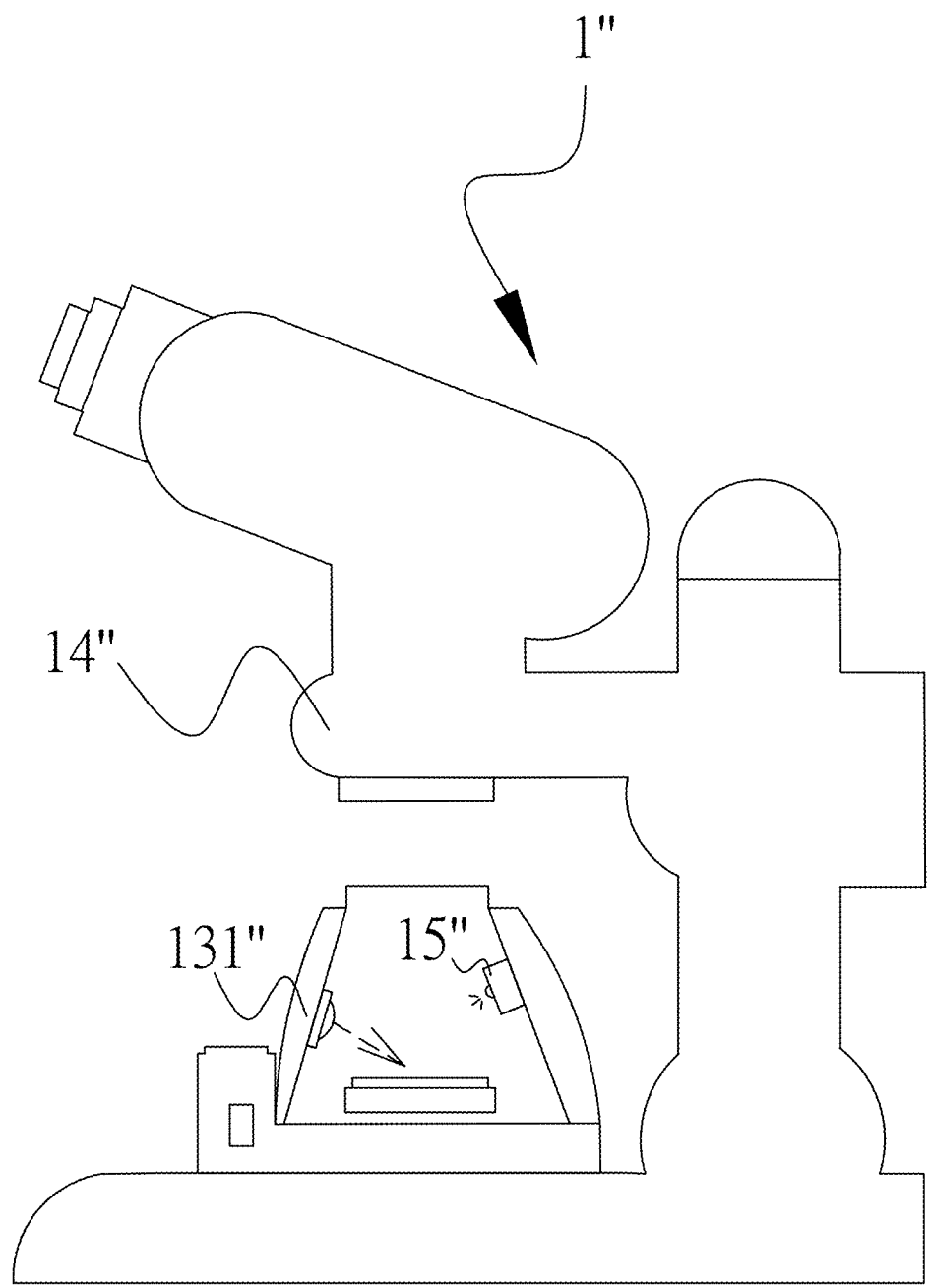
FIG. 5 is a schematic view showing the structure of a fluorescent biological sample operating and monitoring system according to a third preferred embodiment of the present invention.
Figure 6:
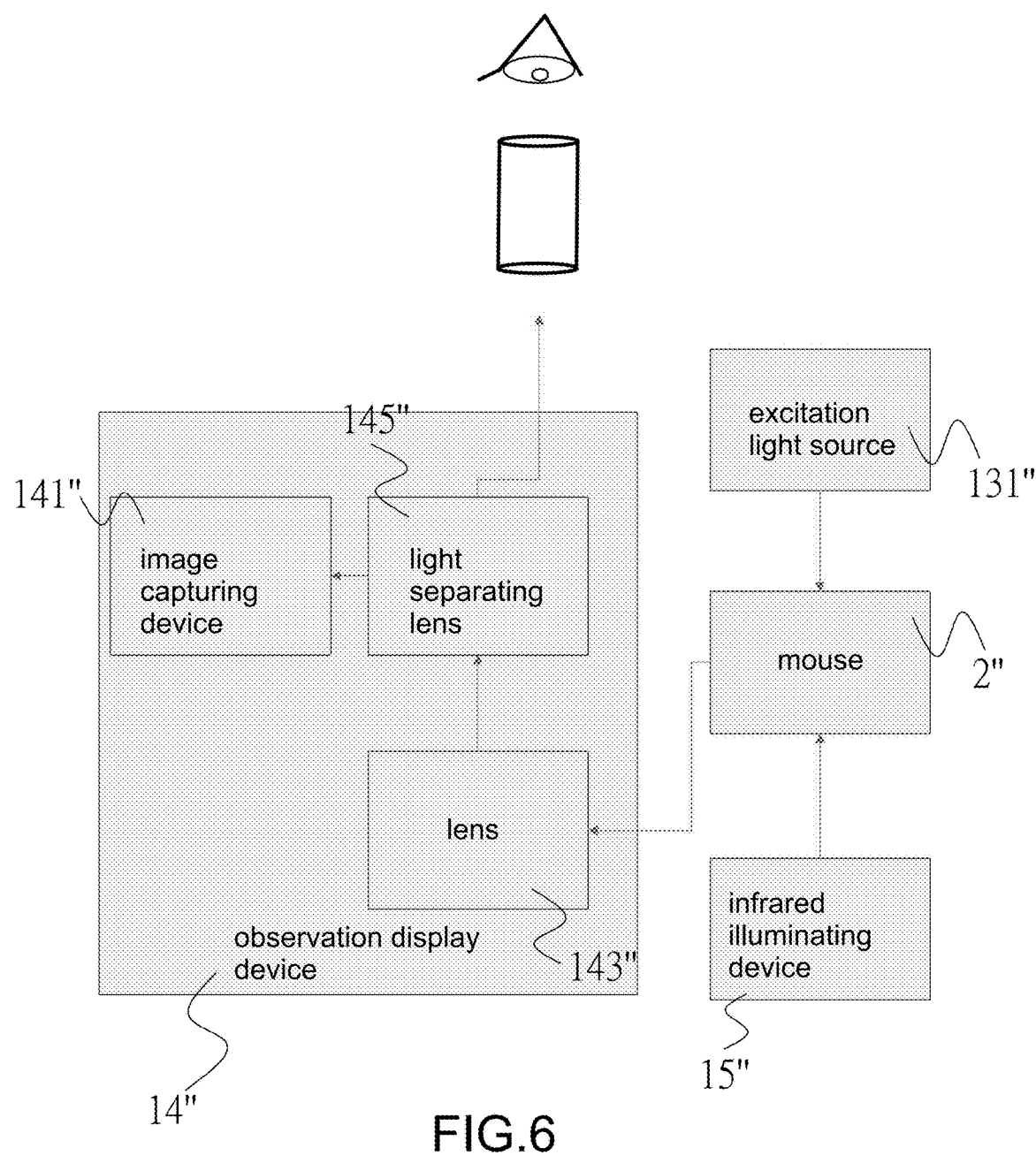
FIG. 6 is a block diagram according to the third preferred embodiment of the present invention, illustrating the relationship among components of an observation display device.

FIGS. 5 and 6 show a fluorescent biological sample operating and monitoring system according to a third embodiment of the present invention. As shown, the observation display device 14" is a microscope with a wavelength encompassing infrared light and visible light, whereas the image capturing device 141" is exemplified as an infrared image sensor. The infrared microscope has a light separating lens interposed between a lens 143" similar to that of the first preferred embodiment and the infrared image sensor. The light separating lens 145" herein separates infrared light from visible light according to wavelength. When the lens 143" acquires an infrared image of a mouse 2" similar to that of the second preferred embodiment through irradiation by the infrared illuminating device 15", the light separating lens 145" will cause the fluorescence excited by the excitation light source 131" to be directly displayed on the goggles as a virtual image, so that the fluorescence image directly enters the eyes of the operator to facilitate observation of the fluorescence response of the mouse 2". On the other hand, the infrared image is displayed on the image display, which is exemplified herein as a screen.

As most existing optical lenses permit direct passage of near-infrared and visible light therethrough, a conventional visible light microscope can be adopted for the microscope exemplified in this embodiment by adding thereto a light separating lens capable of separating infrared, and a simple light sensor to enable the operator to conduct operation in experiments according to images on the screen. Such manner of operation is similar to, for example, a conventional endoscope operation, that is, the progress of experiment can be observed with ease. Furthermore, during the process of operation in experiments, the operator can see through the goggles anytime to observe whether the fluorescent biological sample produces any fluorescence response. Through such improvement, there is no need for a conventional fluorescence microscope that costs at least USD30,000, thereby reducing experimental costs to a considerable extent.

While the invention has been described with reference to the preferred embodiments above, it should be recognized that the preferred embodiments are given for the purpose of illustration only and are not intended to limit the scope of the present invention and that various modifications and changes, which will be apparent to those skilled in the relevant art, may be made without departing from the spirit and scope of the invention.

What is claimed is:

1. A fluorescent biological sample operating and monitoring system for restricting range of movement of at least one fluorescent biological sample so as to facilitate observation of the fluorescent biological sample through the fluorescent biological sample operating and monitoring system, the fluorescent biological sample operating and monitoring system comprising:
   a base formed with a predetermined observation position;
   a shield corresponding to said base and formed with at least one operation opening, said shield cooperating with said base to define a light shielding cavity;
   an infrared illuminating device for illuminating said predetermined observation position with infrared light;
   a low-angle excitation light source device including a plurality of excitation light sources that emit light at a low angle in a direction oriented toward said predetermined observation position, the light emitted by said excitation light sources having a wavelength smaller than the infrared that of light emitted by said infrared illuminating device;
   an observation display device including:
   at least one image capturing device, said image capturing device having a lens disposed in said shield and oriented toward said predetermined observation position for capturing an infrared image; and
   at least one image display for displaying said infrared image of said predetermined observation position captured by said image capturing device to the outside of said shield.

2. The fluorescent biological sample operating and monitoring system according to claim 1, wherein said excitation light source includes a plurality of directional light emitting elements.

3. The fluorescent biological sample operating and monitoring system according to claim 2, wherein said directional light emitting elements are a plurality of light emitting diodes disposed on said base, said shield being formed with a reflecting portion on an inner side thereof for reflecting light beams emitted by said light emitting diodes to said predetermined observation position.

4. The fluorescent biological sample operating and monitoring system according to claim 2, wherein said directional light emitting elements are a plurality of light emitting diodes disposed on said shield.

5. The fluorescent biological sample operating and monitoring system according to claim 1, further comprising a switching device switchable between an operating state and a monitoring state such that, when said switching device is switched to the operating state, said infrared light source being enabled to emit light and said image display displays said infrared image of said predetermined observation position captured by said image capturing device.

6. The fluorescent biological sample operating and monitoring system according to claim 5, wherein said image capturing device is a dynamic camera and has a receivable wavelength range encompassing the wavelength of the infrared light emitted by said infrared illuminating device and the wavelength of fluorescence emitted by the fluorescent biological sample irradiated by said excitation light source.

7. The fluorescent biological sample operating and monitoring system according to claim 1, wherein said image capturing device is a dynamic camera and has a receivable wavelength ranging encompassing the wavelength of the light emitted by said infrared illuminating device, and said image display is an organic light emitting display.

8. The fluorescent biological sample operating and monitoring system according to claim 1, wherein said shield is formed with an observation opening, said observation opening having at least one filter lens disposed thereon for filtering the wavelength of the light emitted by said excitation light source.

9. The fluorescent biological sample operating and monitoring system according to claim 1, wherein said observation display device is an infrared microscope, and said image capturing device includes an infrared image sensor, said infrared microscope including a light separating lens interposed between said lens and said infrared image sensor.

* * * * *